United States Patent [19]
Goulait et al.

[11] Patent Number: 5,482,588
[45] Date of Patent: Jan. 9, 1996

[54] METHOD FOR MANUFACTURING ONE-PIECE TAPE TABS FOR USE WITH DISPOSABLE ABSORBENT ARTICLES

[75] Inventors: David J. K. Goulait; David W. Cabell; Michael T. Huber, all of Cincinnati, Ohio; Karl P. Ronn, Miami, Fla.

[73] Assignee: The Procter & Gamble Company, Cincinnati, Ohio

[21] Appl. No.: 263,322

[22] Filed: Jun. 21, 1994

[51] Int. Cl.$^6$ .......................... B32B 31/18; B32B 31/22; B32B 31/26
[52] U.S. Cl. .......................... 156/264; 156/66; 156/73.1; 156/73.5; 156/209; 156/259; 156/289; 604/389; 604/390
[58] Field of Search .................................. 604/389, 390; 156/66, 259, 264, 289, 209

[56] References Cited

U.S. PATENT DOCUMENTS

| | | | |
|---|---|---|---|
| 3,862,634 | 1/1975 | Small | 604/390 |
| 3,897,293 | 7/1975 | Babcock . | |
| 4,144,887 | 3/1979 | Milnamow | 604/390 |
| 4,491,493 | 1/1985 | Eaton . | |
| 4,531,992 | 7/1985 | Eaton . | |
| 4,576,600 | 3/1986 | Joa | 604/390 |
| 5,004,630 | 4/1991 | Polski . | |
| 5,021,111 | 6/1991 | Swenson | 156/264 |
| 5,106,384 | 4/1992 | Polski . | |
| 5,264,264 | 11/1993 | Shibata et al. | 604/389 X |
| 5,288,546 | 2/1994 | Roessler et al. | 604/389 X |
| 5,322,607 | 7/1994 | Nakamura et al. . | |
| 5,342,685 | 8/1994 | Gobran | 604/389 X |
| 5,399,177 | 3/1995 | Blaney et al. | 604/389 |
| 5,399,219 | 3/1995 | Roessler et al. | 156/259 |

FOREIGN PATENT DOCUMENTS

| | | |
|---|---|---|
| 4-226183 | 8/1992 | Japan . |
| 93/22996 | 11/1993 | WIPO ........................... 604/390 |

*Primary Examiner*—David A. Simmons
*Assistant Examiner*—M. Curtis Mayes
*Attorney, Agent, or Firm*—David M. Weirich; Steven W. Miller; E. Kelly Linman

[57] ABSTRACT

A method for the manufacture of one-piece tape tabs to be used with disposable absorbent articles. The first step is to provide a backing substrate upon which the pressure-sensitive adhesive of the tape tab can be applied. Once the backing is provided, the pressure-sensitive adhesive is applied to regions of one side of the backing substrate. The backing substrate is then slit in a direction parallel to the machine direction forming tape tab stock that is preferably fed directly to the taper unit of the absorbent article manufacturing line. The taper unit cuts the tape tab stock comprising the pressure-sensitive adhesive into individual tape tabs, each having a fixed end and releasable end. The fixed end of each tape tab is joined to the chassis of an absorbent article by means of mechanically bonding the fixed end to the absorbent article. The mechanical bonding not only joins the fixed end of the tape tab to the absorbent article, but also forms a region on the outwardly facing surface of the fixed end of the tape tab that acts as a release surface for the pressure-sensitive adhesive. In preferred embodiments, an area of the absorbent article adjacent to the fixed end of the tape tab is also subjected to mechanical bonding. The mechanical bonding forms a region on the surface of the absorbent article that acts a release surface for the pressure-sensitive adhesive disposed on the releasable end of each tape tab.

17 Claims, 2 Drawing Sheets

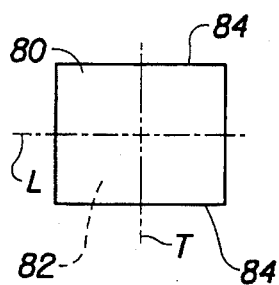
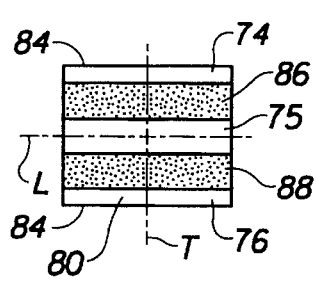
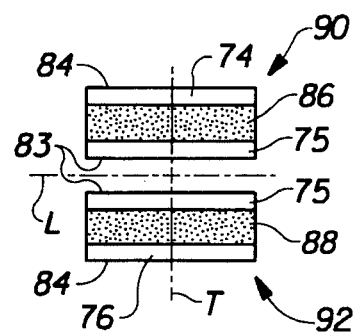
Fig. 3a   Fig. 3b   Fig. 3c
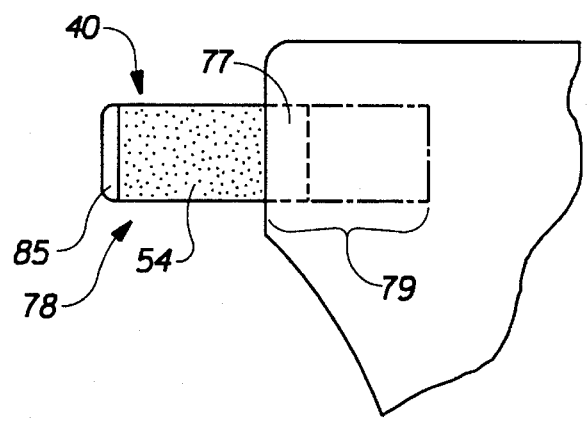
Fig. 4

METHOD FOR MANUFACTURING ONE-PIECE TAPE TABS FOR USE WITH DISPOSABLE ABSORBENT ARTICLES

FIELD OF THE INVENTION

The present invention relates to a method for manufacturing and securing one-piece tape tabs to disposable absorbent articles comprising tape tab closure members, and more particularly to a method for the on-line manufacture and securement of one-piece tape tabs to disposable absorbent articles.

BACKGROUND OF THE INVENTION

Disposable absorbent articles, such as diapers, training pants, incontinence garments, feminine hygiene garments and the like have become very popular in the market place today. Typically, adhesive tape tabs fasteners are used to secure the absorbent articles about the waist of the wearer. Such fasteners are generally manufactured separately from the absorbent articles to which they are attached. For example, it is common for the manufacture of tape tabs to take place in different facilities than the manufacture of the absorbent article chassis, and at a different time. Generally, tape tabs are manufactured by applying a release agent to a backing and winding the backing onto a roll. The roll of backing material treated with a release agent is then unwound and coated with pressure-sensitive adhesive. A release substrate is then generally joined to the backing material comprising the pressure-sensitive adhesive, forming a tape stock. The tape stock is then rewound onto rolls for shipping. Finally, at the place of manufacture of the absorbent article, the tape stock is unwound, cut to size, and joined to the chassis of an absorbent article.

An overriding consideration in the construction of a disposable absorbent article is the cost of manufacturing the absorbent article. The present invention provides a reduced cost method for the manufacture of one-piece tape tabs for use with disposable absorbent articles. The tape tabs can be manufactured "on-line", or concurrently with the chassis of the absorbent articles and in the same location. Therefore, there is no need to rewind the tape stock or prepare it for shipping. This eliminates the need to coat the non-adhesive surface of the tape stock with a release agent, simplifying the process of manufacturing the tape tabs. Further, the one-piece tape tabs of the present invention are joined to the absorbent article in such a way that no release substrate is needed to provide a release surface for the pressure-sensitive adhesive of the tape tab. Thus, the one-piece tape tab of the present invention reduces the overall cost of manufacturing tape tabs and, in turn, disposable absorbent articles.

It is an object of the present invention to provide a low cost method for manufacturing one-piece tape tabs for use with disposable absorbent articles.

It is a further object of the present invention to provide a method for the on-line manufacture of one-piece tape tabs to be used with disposable absorbent articles.

These and other objectives of the present invention will be more readily apparent when considered in reference to the following description and when taken in conjunction with the accompanying drawings.

SUMMARY OF THE INVENTION

The present invention provides a method for the manufacture of one-piece tape tabs to be used with disposable absorbent articles. The tape tabs of the present invention may be manufactured concurrently with the chassis of the absorbent article to which the tape tabs will be attached. The first step is to provide a backing substrate upon which the pressure-sensitive adhesive of the tape tab can be applied. Once the backing is provided, the pressure-sensitive adhesive is applied to regions of one side of the backing substrate. (The pressure-sensitive adhesive preferably functions as the adhesive used to fasten an element of the absorbent article, such as a front waist region, to another element of the absorbent article, such as a rear waist region.) The backing substrate is then slit in a direction parallel to the machine direction forming tape tab stock that is preferably fed directly to the taper unit of the absorbent article manufacturing line. The taper unit cuts the tape tab stock comprising the pressure-sensitive adhesive into individual tape tabs, each having a fixed end and releasable end. The fixed end of each tape tab is joined to the chassis of an absorbent article by means of mechanically bonding the fixed end to the absorbent article. The mechanical bonding not only joins the fixed end of the tape tab to the absorbent article, but also forms a region on the outwardly facing surface of the fixed end of the tape tab that acts as a release surface for the pressure-sensitive adhesive. To reduce the amount of backing substrate needed, and to provide a larger release surface for the releasable end of the tape tab, an area of the absorbent article adjacent to the fixed end of the tape tab is also preferably subjected to mechanical bonding. The mechanical bonding forms a region on the surface of the absorbent article that acts a release surface for the pressure-sensitive adhesive disposed on the releasable end of each tape tab.

This method for the on-line manufacture of a one-piece tape tab provide a very low cost one-piece tape tab. Not only does the method eliminate the need for rewinding the tape stock, and thus the need for a release agent to be applied to the surface of the backing substrate, it also eliminates the need for any release substrate. Therefore, a simplified and more economical process for manufacturing tape tabs for use with disposable absorbent articles is available that uses fewer materials than conventional methods.

BRIEF DESCRIPTION OF THE DRAWINGS

While the specification concludes with claims particularly pointing out and distinctly claiming the subject matter which is regarded as the present invention, it is believed that the invention will be better understood from the following description which is taken in conjunction with the accompanying drawings, in which:

FIGS. 3a–3c represent a plan view of the process for on-line manufacturing tape tabs for use with absorbent articles, showing the flow of the process in the machine direction.

FIG. 4 is a plan view of a portion of an absorbent article comprising the one-piece tape tab manufactured in accordance with the method of the present invention.

DETAILED DESCRIPTION OF THE INVENTION

The method of the present invention is particularly suitable for manufacturing tape tabs for use with disposable absorbent articles. As used herein, the term "absorbent article" refers to devices which absorb and contain body exudates, and more specifically, refers to devices which are placed against the skin of a wearer to absorb and contain the various exudates discharged from the body. The term "disposable" is used herein to describe absorbent articles which are not intended to be laundered or otherwise restored or reused as an absorbent article after a single use (i.e. they are intended to be discarded, and preferably, recycled, composted or otherwise disposed of in an environmentally compatible manner). A "unitary" absorbent article refers to an absorbent article which is formed from separate parts united together to form a coordinated entity so that they do not require separate manipulative parts like a separate holder and liner. A preferred embodiment of a unitary absorbent article comprising tape tabs manufactured by the method of the present invention is the disposable absorbent article shown in FIG. 1. As used herein, the term "diaper" refers to an absorbent article generally worn by infants and incontinent persons that is generally worn about the lower torso of the wearer. It should be understood, however, that the present invention is also applicable to other absorbent articles such as incontinence briefs, diaper holders, feminine hygiene garments, training pants, and the like.

Figure 1:
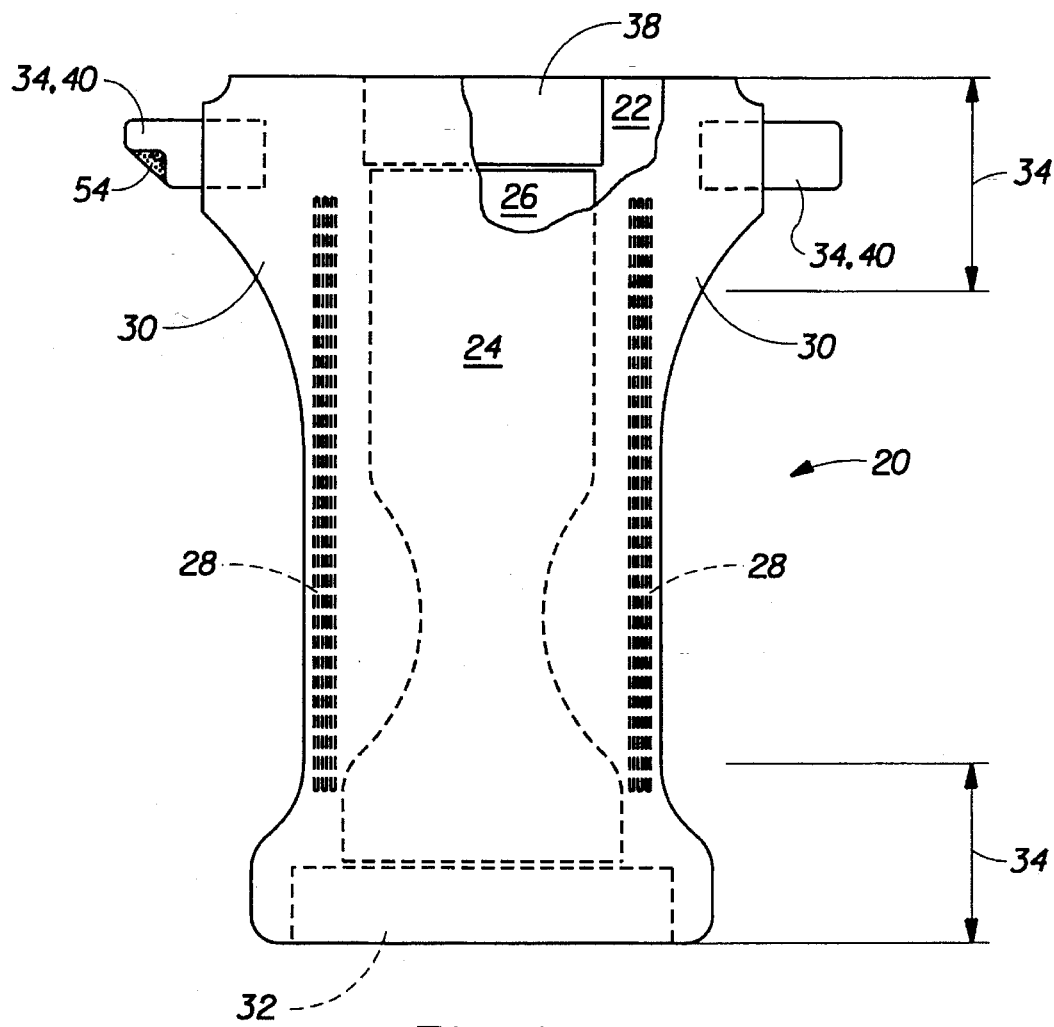
FIG. 1 is a plan view of an absorbent article comprising a tape tab manufactured in accordance with the on-line method of the present invention.

With reference to FIG. 1, an absorbent article, such as diaper 20, generally comprises a liquid permeable topsheet 22, a liquid impermeable backsheet 24, and an absorbent core 26 sandwiched between the topsheet 22 and the backsheet 24. The diaper 20 preferably further comprises a front waist region 36, a rear waist region 38, elasticized leg cuffs 28, ear flaps 30, an elastic waist feature 32 and a fastening system 34 comprising at least one tape tab 40. An example of a preferred absorbent article to which the tape tabs of the present invention may be joined is more fully and completely described in U.S. Pat. No. 5,151,092 entitled "Absorbent Article With Dynamic Elastic Waist Feature Having A Predisposed Resilient Flexural Hinge", issued to Buell et al. on Sep. 29, 1992 which is hereby incorporated by reference herein.

Overall Process for Manufacturing One-Piece Tape Tabs

Figure 2:
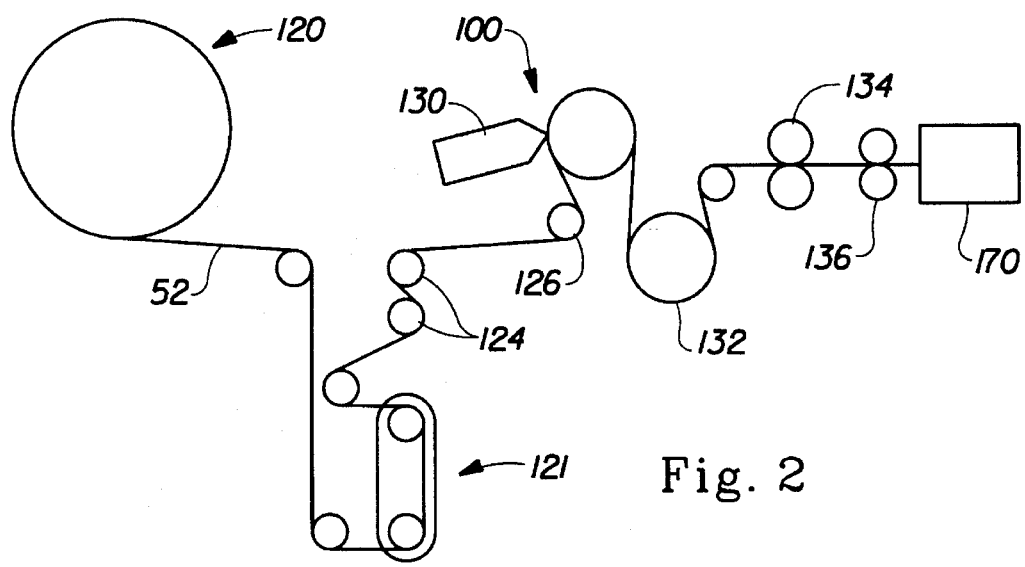
FIG. 2 is a representative side view of the method for on-line manufacturing tape tabs for use with absorbent articles.

The tape tabs 40 of the present invention may be produced on the apparatus 100, as shown in FIG. 2. In a preferred embodiment, the apparatus 100 is integrated into a disposable absorbent article manufacturing line such that the tape tabs 40 of the present invention are manufactured "on-line". (As used herein, the term "integrated" means interconnected process modules that operate concurrently to produce finished products from source materials. The term "on-line" is used to refer to the process of manufacturing the tape tabs 40 of the present invention on an apparatus that is integrated with the manufacturing line that produces the disposable absorbent articles to which the tape tabs will be joined.)

Examining apparatus 100 in greater detail, a backing substrate 52 is provided and taken from the unwind roll 120. The backing substrate 52 may comprise any material to which a pressure-sensitive adhesive may be applied. Some non-limiting examples of suitable backing substrates include films, laminates, woven and non-woven webs, foams, and the like. In a preferred embodiment, the backing substrate 52 comprises a polyolefin or a polyester film ranging in thickness from about 2.5 mils to about 5.0 mils in thickness, more preferably about 4 mils in thickness. A polyolefin film that has been found to be particularly suitable for the backing substrate is the polypropylene film manufactured by the Exxon Chemical Company of Lake Zurich, Ill., under the trade name EX-377.

As shown in FIG. 2, the backing substrate 52 is taken from the unwind roll 120 and preferably passes through a tracking system 121 as is commonly utilized and known in the art to optimally track and adjust the backing substrate 52 into the S-wrap tensioning rolls 124. A tracking system manufactured by the Fife Corporation of Oklahoma City, Okla., and sold as Model Op6 LRA may be suitable. The S-wrap tensioning rolls 124 provide proper tensioning to prevent puckering or bunching of the backing 52.

Guide roll 126 guides the backing 52 into position adjacent the adhesive slot coater 130 for application of the pressure-sensitive adhesive 54. The adhesive slot coater 130 may be any adhesive slot coater as is known in the art. Similarly, the pressure-sensitive adhesive 54 may be any pressure-sensitive adhesive as is known in the art, including, but not limited to the pressure-sensitive adhesives HL-1414 and HL-1350 manufactured by the H. B. Fuller Company of St. Paul, Minn.; and H-2153 manufactured by the Findley Adhesive Corporation of Wauwatosa, Wisc. The adhesive slot coater 130 preferably applies the pressure-sensitive adhesive 54 to the backing 52 in a heated, liquid state. After the pressure-sensitive adhesive 54 is applied, the backing 52 is preferably directed to a chill roll 132 such that the pressure-sensitive adhesive 54 is cooled and permitted to solidify on the surface of the backing 52.

Once the pressure-sensitive adhesive 54 has been applied, and preferably cooled, the backing 52 is preferably directed to a shear slitting apparatus 134 that slits the backing 52 in a direction parallel to the machine direction forming tape tab stock 70. (It should be noted, however, that in a less preferred embodiment, the backing substrate 52 is not slit and separated. In such an embodiment, a single piece of tape tab stock 70 results rather than the multiple segments as described more fully below.) The backing 52 is then separated laterally at the slit. (As used herein, the term "laterally" is defined as the direction perpendicular to the machine direction, or parallel to the cross machine direction.) The backing 52 may be separated by any means as are known in the art, including but not limited to any web spreader 136 known in the art. Finally, the tape tab stock 70 comprising the backing substrate 52 and the pressure-sensitive adhesive 54 is directed to a taper unit 170. The taper unit 170 cuts the tape tab stock 70 into individual tape tabs 40 and joins the individual tape tabs to the chassis of an absorbent article.

Preferred Embodiment

As described above, the tape tabs 40 of the present invention are made by first providing a backing substrate upon which the pressure-sensitive adhesive of the tape tab 40 can be applied. FIG. 3a shows the backing substrate 52 having a longitudinal centerline L and a transverse centerline T perpendicular to the longitudinal centerline L. (As used herein, the term "longitudinal centerline" refers to an imaginary line that runs parallel to the machine direction. The "transverse centerline runs perpendicular to the machine direction and parallel to the cross machine direction.) The backing substrate 52 further comprises a first surface 80, a second surface 82 opposed to the first surface 80, and a pair of outer longitudinal edges 84. (As shown in FIG. 3c, the backing substrate 52 further comprises a pair of inner longitudinal edges 83 once the backing substrate has been slit.)

FIG. 3b shows a plan view of the backing substrate 52 after it has passed the slot coater 130, having the pressure-sensitive adhesive 54 applied to the first surface 80. (The pressure-sensitive adhesive preferably functions as the adhesive used to fasten an element of the absorbent article, such as a front waist region, to another element of the absorbent article, such as a rear waist region.) In a preferred embodiment, the pressure-sensitive adhesive 54 is not applied to the entire first surface 80 of the backing substrate 52. Rather, it is preferred that the pressure-sensitive adhesive 54 be applied continuously to the backing substrate 52 in zones, preferably at least a first zone 86 and a second zone 88. (As used herein, the term "continuously" means a generally unbroken pattern.) The first zone 86 and the second zone 88 are preferably disposed transversely inwardly from the outer longitudinal edges 84 of the backing substrate 52. (As used herein, the term "transversely inwardly" means toward the longitudinal centerline L. The term "transversely outwardly" means away from the longitudinal centerline L.) The area between the outer longitudinal edges 84 of the backing substrate 52 and the zones 86 and 88 of pressure-sensitive adhesive 54 creates fixed regions 74 and 76. (These fixed regions 74 and 76 will be the portions of the tape tabs 40 that become permanently fixed to the chassis of the absorbent article.)

The first zone 86 and the second zone 88 are also preferably transversely separated about the longitudinal centerline L. This leaves a non-adhesive area 75 between the first zone 86 and the second zone 88 that may be utilized as a release tab 85. The release tab 85, as shown in FIG. 4 provides the user with a portion of the backing substrate 52 which is free of pressure-sensitive adhesive 54 and preferably not adhered to the release substrate or any other element of the diaper 20. Thus, the user may grasp the release tab 85 and more easily open the tape tab 40. (As used herein, the phrase "open the tape tab" refers to separating the pressure-sensitive adhesive 54 disposed on the tape tab 40 from the release substrate 50 or any other surface to which the pressure-sensitive adhesive 54 may be adhered.) However, if the first zone 86 and the second zone 88 are not transversely separated about the longitudinal centerline L, alternative methods of providing a release tab 85 are available. The methods include, but are not limited to, folding a portion of the backing substrate 52 adjacent the inner longitudinal edges 83 onto the pressure-sensitive adhesive 54 disposed on the backing substrate 52 or coating the backing substrate 52 adjacent the inner longitudinal edges 83 with a release agent or material that will prevent the pressure-sensitive adhesive 54 in the area adjacent the inner longitudinal edges 83 from adhering to the release surface 79 or any other elements of the diaper 20. (The release surface 79 is described in greater detail below.)

As shown in FIG. 3c, the backing substrate 52 is preferably slit along the longitudinal centerline L, forming at least two backing substrate segments, 90 and 92. (Embodiments are contemplated, however, wherein more than two zones of pressure-sensitive adhesive 54 are applied to the backing substrate and wherein the backing substrate is slit and divided into more than two backing substrate segments.) The backing substrate segments, 90 and 92, are preferably separated transversely before they are directed to the taper unit 170. The taper unit 170 cuts the backing substrate segments 90 and 92 into individual tape tabs 40. Each individual tape tab has a fixed end 77 and a releasable end 78 (shown in FIG. 4). The releasable end 78 preferably comprises the pressure-sensitive adhesive 54 applied to the substrate backing 52. The fixed end 77 preferably comprises one of the fixed regions 74 or 76 of the backing substrate 52 and is preferably free of pressure-sensitive adhesive 54. This reduces the amount of pressure-sensitive used and ensures that the pressure-sensitive adhesive does not interfere with the mechanical bonding of the fixed end 77 to the chassis of the absorbent article.

The fixed end 77 of the tape tab 40 is preferably bonded to a surface of the absorbent article by a mechanical bond. Although any mechanical bonding means as are known in the art may be used, it is preferred that the mechanical bond create a surface that acts as a release surface 79 for the pressure-sensitive adhesive 54 disposed on the releasable end 78 of the tape tab 40. The release surface 79 of the bonded area permits the one-piece tape tab to be releasably fastenable without the use of any release substrate. In preferred embodiments, the area of the release surface 79 is larger than the area of the releasable end 78 tape tab 40 comprising pressure-sensitive adhesive 54. Suitable mechanical bonding methods include, but are not limited to, ultrasonic bonding, autogenous bonding, friction bonding, heat bonding and pressure bonding.

In an especially preferred embodiment of the on-piece tape tab 40, as shown in FIG. 4, the mechanical bond that joins the fixed end 77 of the tape tab to the absorbent article is extended beyond the dimensions of the fixed end 77 of the tape tab 40 onto a surface of the absorbent article adjacent the fixed end 77 of the tape tab 40 to provide a larger release surface 79. This reduces the amount of the tape tab 40 that needs to be reserved for the fixed end 77, and thus, reduces the overall cost of the one-piece tape tab.

The bonded area of the fixed end 77 need only be large enough to ensure that the tape tab 40 will be securely fixed to the absorbent article once the mechanical bonding process is complete. The fixed end 77 of the tape tab 40 may be joined to the top sheet 22 or the backsheet 24 of the absorbent article. Further, the fixed end may be joined between the topsheet 24 and the backsheet 26, or to any other element of the absorbent article. One preferred embodiment is shown in FIG. 4, wherein the fixed end 77 of the tape tab 40 is joined to the topsheet 24 of the absorbent article.

In alternative embodiments of the present invention, the release surface 79 may be formed by mechanical manipulation of the fixed regions 74 and 76 of the tape tab stock 70 before the tape tab stock 70 is cut into individual tape tabs 40, after individual tape tabs 40 have been formed but before the tape tabs 40 are joined to the absorbent article, or after the tape tabs 40 are joined to the absorbent article. (As used herein, the term "mechanical manipulation" refers to the process of changing the physical attributes of a substance by means including, but not limited to, heat, pressure, friction, ultrasonics or embossing.) In these embodiments, the fixed ends 77 of the tape tabs 40 may be joined to the absorbent article by methods other than mechanical bonding, including, but not limited to, adhesive bonding. An adhesive suitable for bonding the tape tabs 40 the an absorbent article is the hot melt adhesive HL-1358 manufactured by the H.B. Fuller Company of St Paul, Minn.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for manufacturing a refastenable, one-piece tape tab for a disposable absorbent article, comprising the steps of:

providing a backing substrate;

applying a pressure-sensitive adhesive to said backing substrate forming a tape tab stock;

cutting said tape tab stock into individual tape tabs, each said tape tab having a fixed end and a refastenable end;

bonding said fixed end of said tape tab to an absorbent article having a topsheet and a backsheet, said bonding forming an area to which said pressure-sensitive adhesive can be releasably attached; and mechanically manipulating a portion of said absorbent article adjacent to said fixed end of said tape tab creating a release surface such that said refastenable end of said tape tab can be releasably attached to said release surface.

2. The method of claim 1 wherein said bonding step comprises a bonding method selected from the following group: ultrasonic bonding, heat bonding, pressure bonding, friction bonding or autogenous bonding.

3. The method of claim 1 wherein said pressure-sensitive adhesive is not applied to said fixed end of said tape tab.

4. The method of claim 1 wherein said fixed end is bonded to said topsheet, said backsheet or between said topsheet and said backsheet of said absorbent article.

5. The method of claim 1 wherein said backing substrate comprises a polypropylene film.

6. A method for manufacturing a refastenable, one-piece tape tab for a disposable absorbent article, comprising the steps of:

providing a backing substrate having a longitudinal centerline and a transverse centerline perpendicular to said longitudinal centerline;

applying a pressure-sensitive adhesive to said backing substrate;

slitting said backing substrate in a direction parallel to said longitudinal centerline to form at least two segments;

separating said segments in a direction parallel to said transverse centerline forming a tape tab stock;

cutting said tape tab stock into individual tape tabs, each said tape tab having a fixed end and a refastenable end;

bonding said fixed end of said tape tab to an absorbent article having a topsheet and a backsheet, said bonding forming an area to which said pressure-sensitive adhesive can be releasably attached; and mechanically manipulating a portion of said absorbent article adjacent to said fixed end of said tape tab creating a release surface such that said refastenable end of said tape tab can be releasably attached to said release surface.

7. The method of claim 6 wherein said step of slitting said backing substrate comprises slitting said backing substrate coincident with said longitudinal centerline.

8. The method of claim 6 wherein said bonding step comprises a bonding method selected from the following group: ultrasonic bonding, heat bonding, pressure bonding, friction bonding or autogenous bonding.

9. The method of claim 6 wherein said pressure-sensitive adhesive is not applied to said fixed end of said tape tab.

10. The method of claim 6 wherein said fixed end is bonded to said topsheet, said backsheet or between said topsheet and said backsheet of said absorbent article.

11. The method of claim 6 wherein said backing substrate comprises a polypropylene film.

12. A method for manufacturing a refastenable, one-piece tape tab for a disposable absorbent article, comprising the steps of:

providing a backing substrate;

applying a pressure-sensitive adhesive to said backing substrate forming a tape tab stock;

mechanically manipulating at least a portion of said backing substrate to form a release surface to which said pressure-sensitive adhesive may be releasably attached, cutting said tape tab stock into individual tape tabs, each said tape tab having a fixed end and a refastenable end; and joining said fixed end of said tape tab to an absorbent article;

wherein said step of mechanically manipulating at least a portion of said backing substrate is performed alter said tape tab stock is cut into said individual tape tabs.

13. A method for manufacturing a refastenable, one-piece tape tab for a disposable absorbent article, comprising the steps of:

providing a backing substrate;

applying a pressure-sensitive adhesive to said backing substrate forming a tape tab stock;

mechanically manipulating at least a portion of said backing substrate to form a release surface to which said pressure-sensitive adhesive may be releasably attached;

cutting said tape tab stock into individual tape tabs, each said tape tab having a fixed end and a refastenable end;

joining said fixed end of said tape tab to an absorbent article;

wherein said step of mechanically manipulating at least a portion of said backing substrate is performed after said tape tabs are joined to said absorbent article.

14. A method for manufacturing a refastenable, one-piece tape tab for a disposable absorbent article, comprising the steps of:

providing a backing substrate;

applying a pressure-sensitive adhesive to said backing substrate forming a tape tab stock;

mechanically manipulating at least a portion of said backing substrate to form a release surface to which said pressure-sensitive adhesive may be releasably attached;

cutting said tape tab stock into individual tape tabs, each said tape tab having a fixed end and a refastenable end;

joining said fixed end of said tape tab to an absorbent article; and mechanically manipulating a portion of said absorbent article adjacent to said fixed end of said tape tab creating a release surface such that said refastenable end of said tape tab can be releasably attached to said release surface.

15. The method of claim 14 wherein said fixed end of each of said tape tabs is joined to said absorbent article by an adhesive.

16. The method of claim 15 wherein said adhesive comprises a hot melt adhesive.

17. The method of claim 14 wherein step of mechanically manipulating said backing substrate comprises a method selected from the following group: heat manipulation, pressure manipulation, ultrasonic manipulation, friction manipulation or manipulation resulting from embossing said backing substrate.

* * * * *